(12) United States Patent
Milella

(10) Patent No.: US 12,330,222 B2
(45) Date of Patent: Jun. 17, 2025

(54) SHAFT RETENTION MECHANISM

(71) Applicant: ECA MEDICAL INSTRUMENTS, Thousand Oaks, CA (US)

(72) Inventor: Michael J. Milella, Thousand Oaks, CA (US)

(73) Assignee: ECA Medical Instruments, Thousand Oaks, CA (US)

( * ) Notice: Subject to any disclaimer, the term of this patent is extended or adjusted under 35 U.S.C. 154(b) by 776 days.

(21) Appl. No.: 17/610,137

(22) PCT Filed: May 9, 2019

(86) PCT No.: PCT/US2019/031622
§ 371 (c)(1),
(2) Date: Nov. 9, 2021

(87) PCT Pub. No.: WO2020/226661
PCT Pub. Date: Nov. 12, 2020

(65) Prior Publication Data
US 2022/0212321 A1  Jul. 7, 2022

(51) Int. Cl.
*B23B 31/08* (2006.01)
*B23B 31/20* (2006.01)

(52) U.S. Cl.
CPC ............ *B23B 31/083* (2013.01); *B23B 31/20* (2013.01); *B23B 2231/58* (2021.01); *Y10T 279/17179* (2015.01)

(58) Field of Classification Search
CPC ..... B23B 31/083; B23B 31/086; B23B 31/20; B23B 31/201; B23B 2231/58; Y10T 279/17153; Y10T 279/17179
See application file for complete search history.

(56) References Cited

U.S. PATENT DOCUMENTS 3,316,576 A * 5/1967 Urbush .................. A61C 17/40
279/23.1
5,820,136 A * 10/1998 Han .................... B23B 31/2073
279/46.9

(Continued)

FOREIGN PATENT DOCUMENTS

DE    102012000437 A1   7/2012
EP    2623266            8/2013

OTHER PUBLICATIONS

International Search Report, issued in PCT/US2019/031622, mailed Jul. 25, 2019.

(Continued)

*Primary Examiner* — Eric A. Gates
(74) *Attorney, Agent, or Firm* — Ferguson Case Orr Paterson LLP

(57) ABSTRACT

A retention assembly for connecting a base to a tool having a shaft includes a shaft engagement socket defining a shaft receptacle configured to receive the shaft; a retainer configured to secure the shaft to the shaft engagement socket, the retainer having a body with an opening that can receive the shaft; and at least one finger extending from the body, defining a sliding surface, and being configured to contact the shaft. The sliding surface can contact a ramp on the shaft retainer socket, and the retainer can translate relative to the shaft engagement socket, such that when it is translated toward the shaft engagement socket, the sliding surface slides along the ramp and causes the finger to move away from the shaft, and when the retainer is translated away from the shaft engagement socket, the sliding surface slides along the ramp and causes the finger to move towards the shaft.

11 Claims, 20 Drawing Sheets

(56) References Cited

U.S. PATENT DOCUMENTS

| | | | |
|---|---|---|---|
| 7,284,936 B1 | 10/2007 | Rinner | |
| 8,523,873 B2 * | 9/2013 | Bharadwaj | A61B 17/1757 600/554 |
| 2009/0056512 A1 | 3/2009 | Chen | |
| 2010/0030282 A1 | 2/2010 | Ciccone | |
| 2012/0189979 A1 | 7/2012 | Tanake | |

OTHER PUBLICATIONS

Written Opinion, issued in PCT/US2019/031622, mailed Jul. 25, 2019.
EPO Communication Pursuant to Rules 70(2) and 70a(2) EPC Issued in European Application 19927936.5, Dated Aug. 16, 2023.
Supplementary European Search Report Issued in EP Application No. 19927936.5, Dated Jul. 5, 2023.
European Search Opinion Issued in EP Application No. 19927936.5, Dated Jul. 5, 2023.
EPO Communication Pursuant to Rules 161(2) and 162 EPC of Application No. 19927936.5, Dated Aug. 22, 2022.

* cited by examiner

SHAFT RETENTION MECHANISM

RELATED APPLICATION

This is a national phase application of International Patent Application No. PCT/US2019/031622, filed on May 9, 2019. The international application referenced in this paragraph is incorporated by reference as if set forth fully herein.

TECHNICAL FIELD

This disclosure generally relates to devices and methods for connecting a tool having a shaft to a base, and more particularly relates to a new design for connecting and, retaining a tool having a shaft in engagement with a socket.

BACKGROUND

Rotary tools are often used in many fields for precise applications. The spectrum of bases, mounts and handles for interchangeable tools is broad. A commonality on both mechanical and powered devices or bases is the ability to mount and unmount a tool. The bases or handles may be fixed wherein t e base provides on a fixation point, other bases may include additional mechanism for any or ratcheting, torque control and the like. There are shortcomings with conventional connecting mechanisms. First, existing devices have many separate components. This makes them difficult to assemble and costly to manufacture. Second, existing options which are intended for many repetitive uses and require proper maintenance and sterilizations between uses. In medical uses, they may contact dangerous medical waste, requiring extensive cleaning and sterilization and carrying an inherently higher risk of contamination. Therefore, there is a need for an improved retention assembly for connecting a tool.

SUMMARY DESCRIPTION

The foregoing needs are met by the various aspects of retainer assemblies disclosed. A retention assembly for connecting a base to a tool having a shaft can include a shaft engagement socket that defines a shaft receptacle configured to receive the shaft along an insertion axis. The retention assembly includes a retainer configured to releasably secure the shaft to the shaft engagement socket. The retainer has a body that defines an opening extending therethrough, with the opening being dimensioned to receive the shaft. The retention assembly further includes at least one finger extending from the body of the retainer.

On some non-limiting aspects, the at least one finger may define a sliding surface and be configured to contact the shaft. The sliding surface of the at least one finger may be configured to slidably contact a ramp on the shaft retainer socket.

The retainer may be movable relative to the shaft engagement socket along the insertion axis, such that when the retainer is translated toward the shaft engagement socket, the sliding surface of the at least one finger slides along the ramp of the shaft engagement socket and causes the at least one finger to move away from the shaft, and when the retainer is translated away from the shaft engagement socket, the sliding surface of the at least one finger slides along the ramp and causes the at least one finger to move towards the shaft.

According to a non-limiting aspect of the disclosure, the at least one finger may include a protrusion between the sliding surface and the body of the retainer. The protrusion may extend from the at least one finger towards the insertion axis and be configured to be received within a notch on the shaft. When the protrusion is in the notch, the shaft may be precluded from moving along the insertion axis. This would help solve the problem of an unsecured shaft or of a shaft that is accidentally or inadvertently removed from the retention assembly.

According to a non-limiting aspect, the retainer may include an outer wall extending from the body and an attachment clip disposed on the outer wall. The attachment clip may be configured to slidably engage the shaft engagement socket to releasably secure the retainer to the shaft engagement socket. The retainer may be removed from the rest of the device and used reused later or disposed of. Removing the retainer may help reduce contamination from improperly cleaned retainers by allowing the retainer to be cleaned or replaced.

In some non-limiting aspects, the body of the retainer may include a cutout between the at least one finger and the outer wall.

According to some aspects, the body may include a plurality of cutouts between the at least one finger and the outer wall.

According to a non-limiting aspect, the shaft engagement socket may include at least one wall configured to contact a locking surface on a socketing region of the shaft when the socketing region is in the shaft engagement socket. When the wall is in contact with the locking surface, rotational movement of the shaft around the insertion axis may be precluded. This may be advantageous to properly impart rotational force from the base or another rotary mechanism configured to rotate the shaft.

In some aspects, the socketing region of the shaft may have a semi-circular cross section.

In some aspects, the shaft engagement socket may include four walls, each wall being orthogonal to two adjacent walls. The four walls may define the shaft receptacle that is configured to receive the shaft. The proximal end of the shaft may have a rectangular cross section in this aspect.

According to a non-limiting aspect, the at least one finger of the retention assembly may be deformable, such that when the retainer is translated towards the shaft engagement socket, the at least one finger deflects radially away from the insertion axis.

In some aspects, the protrusion may be triangular, and the notch on the shaft may also be triangular.

In other aspects, the protrusion may be arcuate, and the notch on the shaft may be arcuate.

In a non-limiting aspect, the retainer may include a plurality of fingers as described herein.

In some aspects, the retainer may include at least three fingers.

In sonic aspects, the retainer may include four fingers.

According to a non-limiting aspect, the shaft, engagement socket may define a radial channel having a floor and a ceiling. The radial channel may be configured to receive the attachment clip therein. The attachment clip may be movable within the channel between the floor and the ceiling, such that the movement of the retainer towards the shaft engagement socket is confined by contact between the attachment clip and the ceiling, and movement away from the shaft engagement socket is confined by contact between the attachment clip and the floor.

According to a non-limiting aspect, the retainer may define a guide configured to contact the shaft and to align the shaft to a permitted orientation. The shaft may be precluded from moving through the retainer if the shaft is not in the permitted orientation. This may help reduce improper insertion of the shaft into the retention assembly and can also reduce instances of damage to the shaft or to the retainer. This would reduce associated manufacturing costs and preparation time during use.

In some non-limiting aspects, the tool having the shaft that is connected to the retention assembly may be a medical device.

In some non-limiting aspects, the retainer may be disposable and unsuitable for heat sterilization.

According to an aspect of the disclosure, a method of connecting a tool having a shaft to a base may include the step of inserting a shaft into an opening defined by a retainer. The retainer has at least one finger configured to contact the shaft. The method further includes the step of moving the at least one finger away from the shaft such that the shaft passes through the opening of the retainer and towards a shaft retention socket. The method further includes the step of inserting the shaft into a shaft receptacle defined by the shaft retention socket. The method also includes securing the shaft within the shaft receptacle by moving the at least one finger towards the shaft such that the at least one finger precludes translation of the shaft along the insertion axis.

According to a non-limiting aspect, the method may further include the step of moving the retainer in a first direction along the insertion axis toward the shaft engagement socket. This can result in the at least one finger being moved away from the shaft.

According to a non-limiting aspect, the method may further include the step of sliding the at least one finger along a ramp defined by the shaft engagement socket when the retainer is moved along the insertion axis.

According to a non-limiting aspect, the method may further include removing the shaft from the base. The removal step may include moving the at least one finger away from the shaft and moving the shaft out of the shaft receptacle and away from the shaft engagement socket.

In some aspects, the method may include a further step of precluding rotational movement of the shaft when the shaft is within the shaft receptacle. This may be performed by contacting a wall defined by the shaft receptacle with a corresponding locking surface on the shaft. This may be advantageous to properly impart rotational force from the base or another rotary mechanism configured to rotate the shaft.

According to a non-limiting aspect, the method may further include the step of orienting the shaft to a permitted orientation by contacting the shaft to a guide defined on the retainer. This may help reduce improper insertion of the shaft into the retention assembly and can also reduce instances of damage to the shaft or to the retainer. This would reduce associated manufacturing costs and preparation time during use.

According to a non-limiting aspect, the method may further include a step of contacting a protrusion extending from the at least one finger with a notch defined on the shaft. When the at least one finger is moved away from the shaft, the protrusion is also moved out of the notch, and when the at least one finger is moved toward the shaft, the protrusion is moved into the notch.

According to a non-limiting aspect of the present disclosure, a retention assembly for connecting a base to a tool having a shaft may include a shaft engagement socket having four walls, each wall being orthogonal to two adjacent walls. The four walls may define a shaft receptacle. The shaft engagement socket may be configured to receive the shaft of the medical tool. In some instances the shaft engagement socket may be configured to correspond to the cross section of the shaft. The shaft has a proximal end and a distal end opposite the proximal end and defines an insertion axis extending between the proximal end and the distal end. The shaft receptacle of the shaft engagement socket may be dimensioned to slidably receive the proximal end of the shaft therein. A retainer may be configured to removably secure the shaft to the socket. The retainer may have a body that defines an opening extending therethrough, the opening being dimensioned to receive the proximal end of the shaft therein. The retainer further may have an outer wall extending from the body, A deformable clip may be disposed on the outer wall and be configured to slidably engage the shaft engagement socket to releasably secure the retainer to the shaft engagement socket. The deformable clip may be deformable in a direction orthogonal to the insertion axis. A finger may be disposed on the inner wall and configured to deflect away from the insertion axis. The finger may define a sliding surface and a protrusion disposed between the contact surface and the body of the retainer. The protrusion may extend from the finger towards the insertion axis and be configured to contact a notch defined on the shaft. A guide may be disposed on the retainer. The guide may be configured to contact the shaft and to orient the shaft to a permitted orientation. The guide may preclude the shaft from moving into the retainer if the shaft is not in the permitted orientation. Each wall of the shaft engagement socket may define a ramp configured to slidably contact the contact surface of the finger. The retainer may be configured to translate relative to the shaft engagement socket along the insertion axis. When the retainer is translated toward the shaft engagement socket, the sliding surface of the finger slides along the ramp of the shaft engagement socket and causes the finger to deflect away from the insertion axis. The proximal end of the shaft may define a rectangular cross section and may be insertable into the shaft receptacle of the shaft engagement socket, such that when the proximal end is in the shaft receptacle, rotational movement of the shaft about the insertion axis is impeded.

DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In the drawings.

Figure 19:
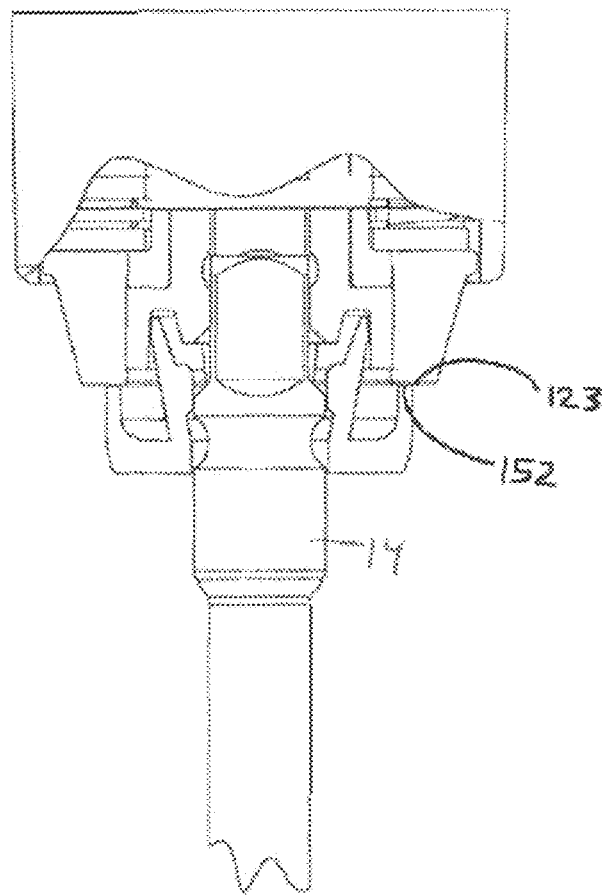
Figure 20:
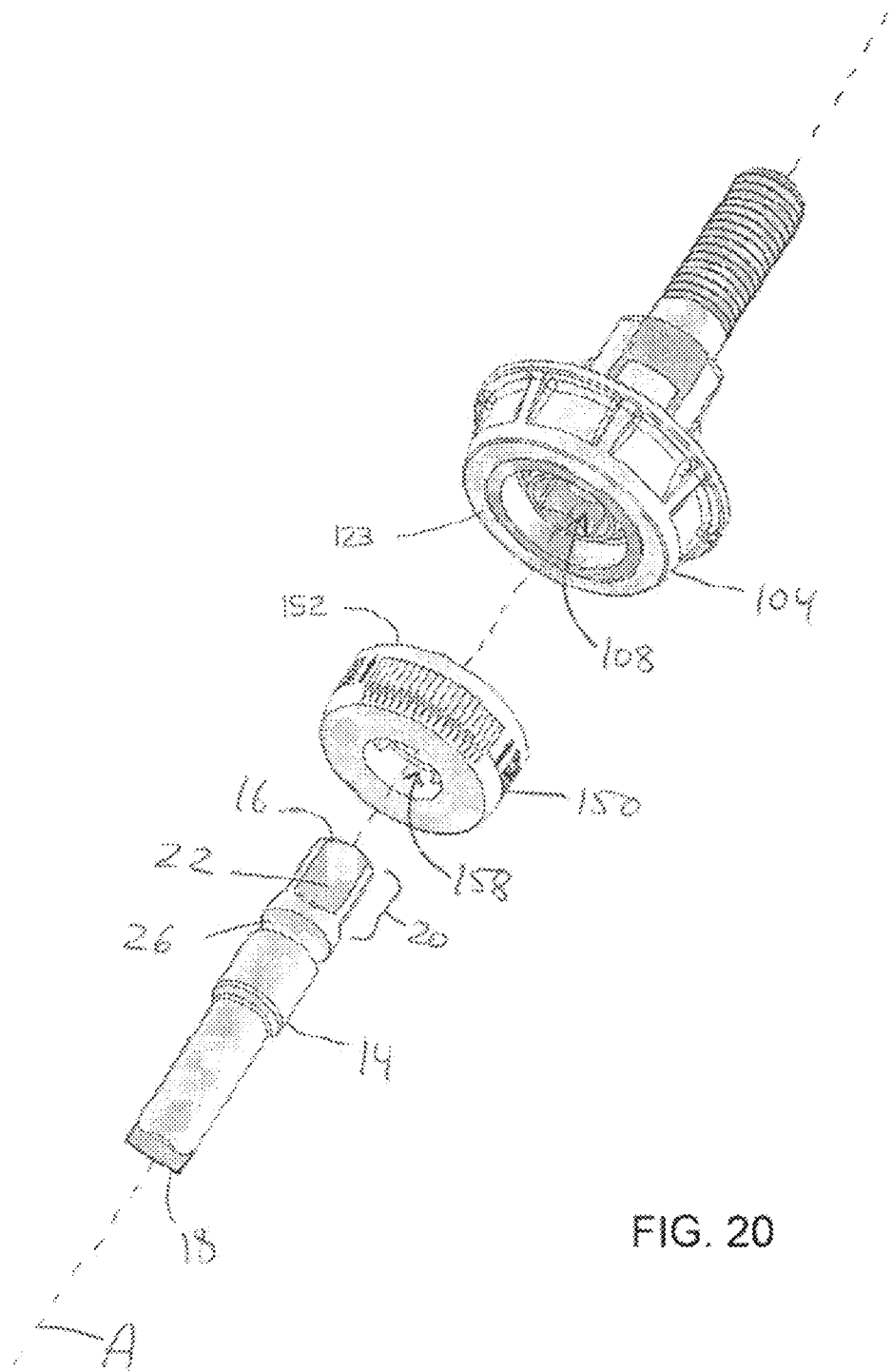

FIG. 19 illustrates a cross-sectional view of a retention assembly according to an aspect of the disclosure depicting an alternate attachment means of the retainer and the shaft engagement socket; and FIG. 20 illustrates an exploded isometric view of a retention assembly according to an aspect of the disclosure and showing an alternate attachment means of the retainer and the shaft engagement socket.

Aspects of the disclosure will now be described in detail with reference to the drawings, wherein like reference numbers refer to like elements throughout, unless specified otherwise.

FURTHER DESCRIPTION

Bases which hold tools are used across various industries, including medical. The tools often need to be connected or disconnected. The bases include the full spectrum of devices from fixed to rotating, including but not limited to ratcheting, drills, motors, and torque limiting. A base can have a retention assembly attached thereto that serves to connect and disconnect a desired tool. While torque-limiting devices are exemplified throughout this disclosure, it will be understood that such an engagement assembly is not limited only to torque-limiting devices, but also includes other bases and devices and other power or rotary tools and apparatuses used in tool automation. Similarly, this disclosure is not limited to any particular tool that is connected to the base, and it will be appreciated that any rotational tool can be implemented, such as a drill, driver, cutter, grinder, sander, or another rotational apparatus.

Figure 1:
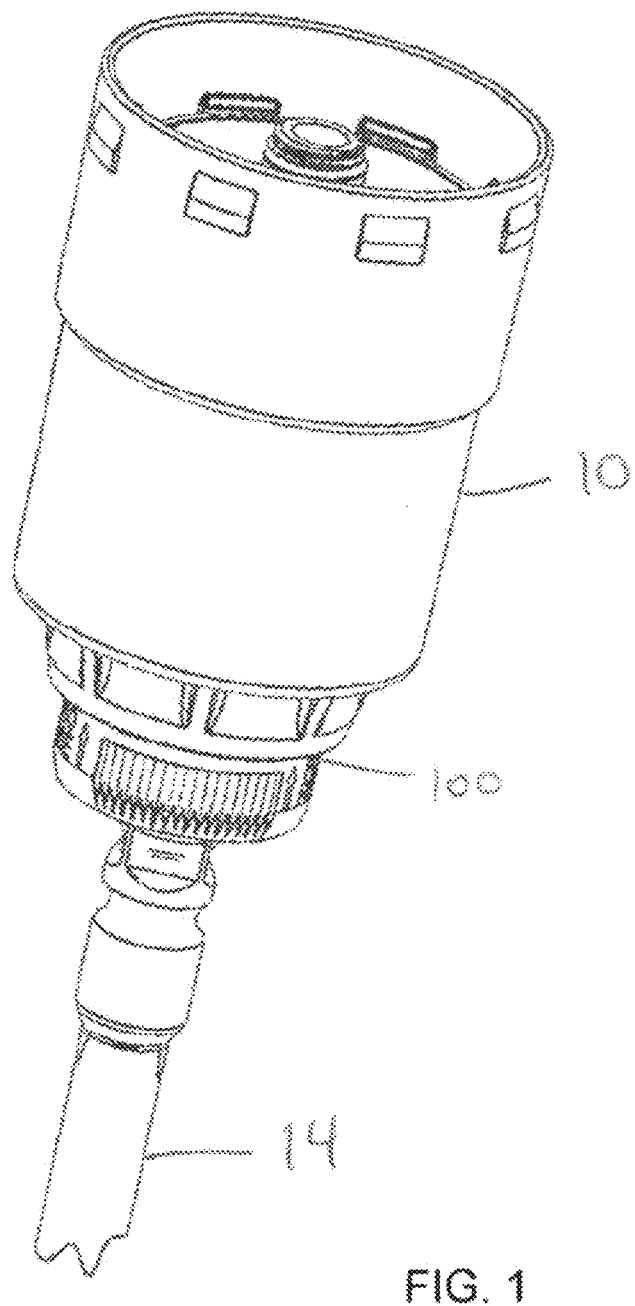
FIG. 1 illustrates an isometric view of a base engaged with a shaft according to an aspect of the present disclosure.
Figure 2:
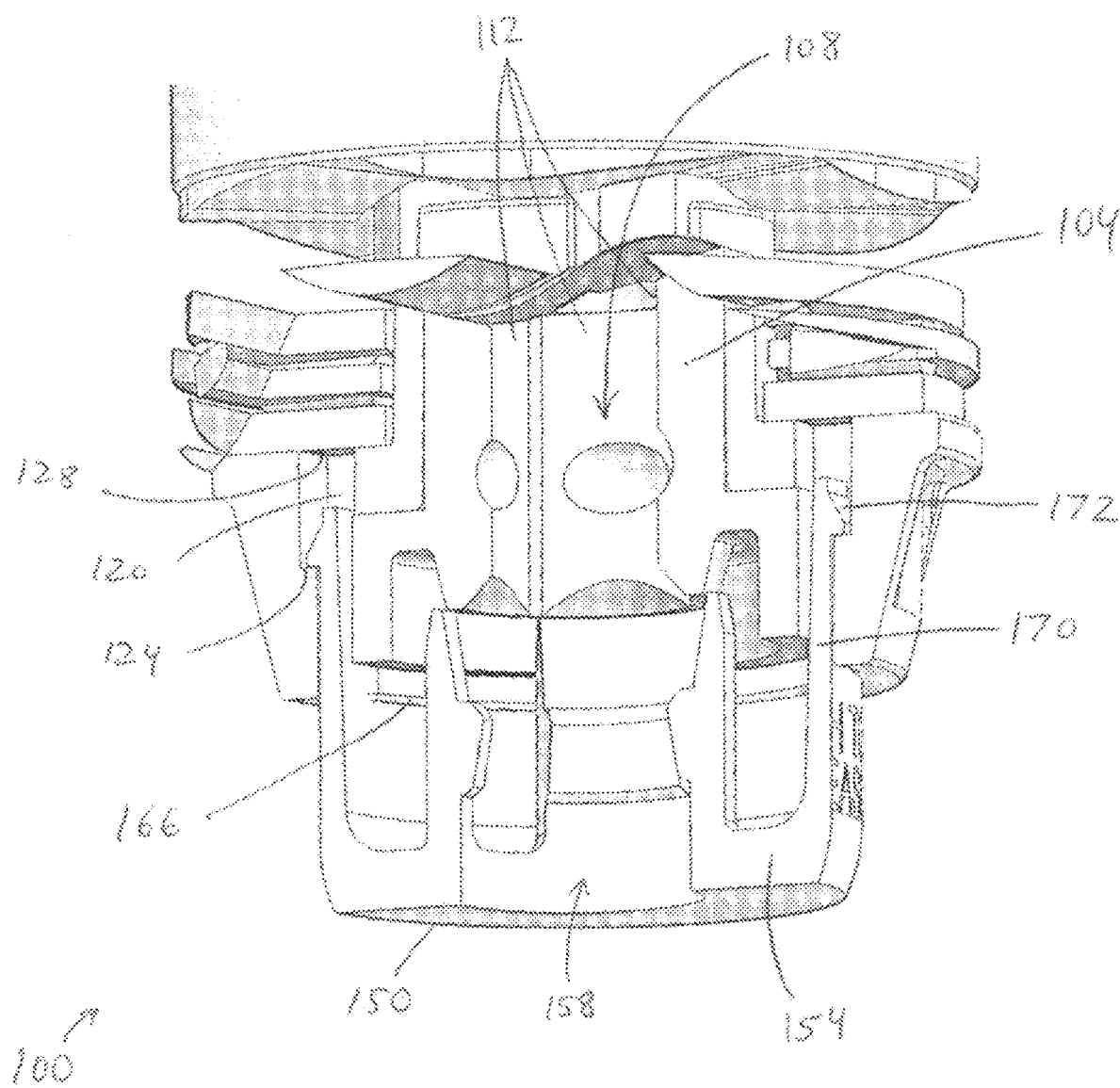
FIG. 2 illustrates an isometric cross-sectional view of a retention assembly according to an aspect.
Figure 3:
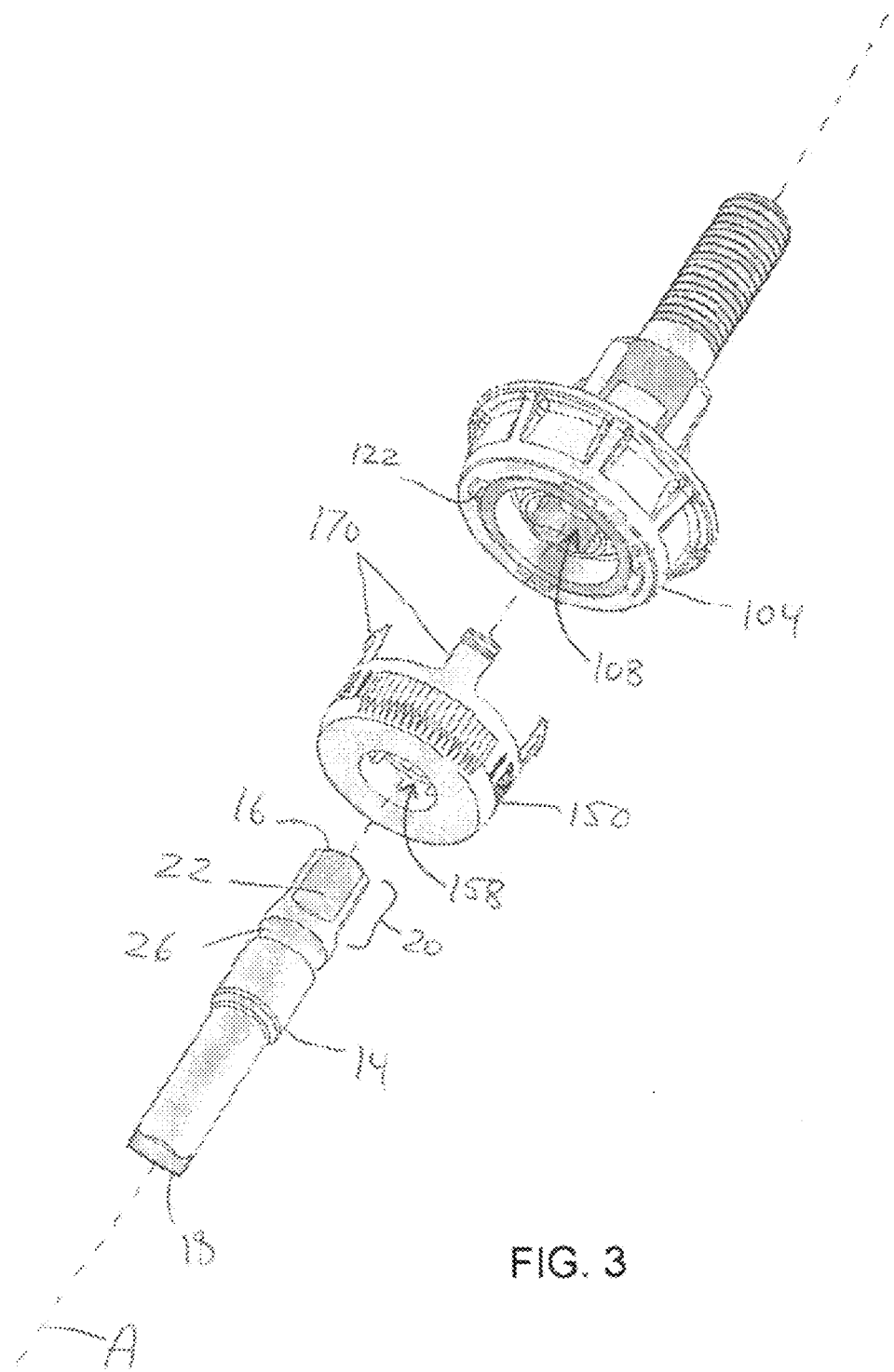
FIG. 3 illustrates an exploded isometric view of a retention assembly and a shaft.

Referring to FIG. 1, a device 10 includes a retention assembly 100 that is configured to receive and interact with a tool having a shaft 14. The shaft 14 can be inserted into the retention assembly 100 and releasable secured therein. While secured by the retention assembly 100, the shaft 14 can receive rotational force from the torque-limiting device 10 and further impart that force onto the connected tool (not shown). The shaft 14 has a proximal end 16 and a distal end 18 opposite the proximal end 16. The shaft 14 can be connected to a rotational tool (not shown) at the distal end 18. A socketing region 20 is defined along the shaft closer to the proximal end 16 than to the distal end 18. The socketing region 20 may be directly adjacent to the proximal end 16.

With reference to FIGS. 2-5, the retention assembly 100 has a shaft engagement socket 104 that is configured to retain the shaft 14 and to provide an interface between the shaft 14 and the base 10. The shaft engagement socket 104 includes at least one wall 112 that defines a shaft receptacle 108, into which the proximal end 16 of the shaft 14 can be inserted along an insertion axis A. The shaft engagement and the shaft are configured to provide a shape for the shaft engagement which receives a cross-section of the shaft. The shaft may be circular, D-shaped (semi-circular), hexagon, polygon or another shape formed in cross section on a shaft. In some aspects, the shaft receptacle 108 may be defined by a plurality of walls 112 arranged in an advantageous geometric shape. For example, the shaft engagement socket 104 may include four walls 112, with each wall being disposed orthogonally to each adjacent wall such that the defined shaft receptacle 108 has a square cross section. The cross section of the shaft receptacle 108 may complement that of the socketing region 20 of the shaft 14. While square cross sections are exemplified, it will be appreciated by persons skilled in the art that other suitable shapes can be used, such as semi-circles, rectangles, pentagons, hexagons, or other polygons. The socketing region 20 may include at least one locking surface 22 configured to contact the wall 112 when the shaft 14 is in the shaft receptacle 108. The cross section of the shaft receptacle 108 may be the same shape as that of the socketing region 20, but that is not a requirement.

When rotational force is imparted by the base 10 or by another driver to the shaft 14, it is advantageous to prevent the shaft 14 from rotating freely within the shaft receptacle 108 or to prevent the shaft engagement socket 104 from rotating freely around the shaft 14 without imparting the desired rotational force. Contact between at least one wall 112 and at least one locking surface 22 is configured to confine the link the rotation of the shaft 14 with that of the shaft engagement socket 104.

To prevent the shaft 14 from being inadvertently removed from the shaft engagement socket 104, a retainer 150 secures the shaft 14 within the shaft receptacle 108. Referring to FIGS. 4-12, the retainer 150 has a body 154 that defines an opening 158 therethrough. The opening 158 is dimensioned such that at least a portion of the shaft 14, including at least the socketing region 20, can be inserted through it. The retainer 150 includes at least one finger 200 that surrounds the opening 158. The finger 200 is configured to engage with the shaft 14 and to prevent the shaft 14 from being removed from the shaft receptacle 108.

The finger 200 extends from the body 154 and includes a sliding surface 204 and a protrusion 208 between the sliding surface 204 and the body 154. The retention assembly 100 may include any suitable number of fingers 200, for example, 1, 2, 3, 4, ... or 20 fingers 200.

Each finger 200 can be configured to move toward and away from the insertion axis A as the shaft 14 is inserted into or removed from the shaft engagement socket 104. The finger 200 may include an elastically deformable material and may be permanently attached to, or be a unitary part of, the retainer body 154. As a force is applied to the finger 200 radially away from the insertion axis A, the finger 200 may remain fixed to or a part of the body 154, while the sliding surface 204 and the protrusion 208 may be deflected radially away from the insertion axis A. When the force is removed, the finger 200 reverts to its previous non-deflected state, and the sliding surface 204 and the protrusion 208 are moved radially toward the insertion axis A.

In some aspects, the finger 200 may be a non-unitary part that is separated from the body 154 and is moveably attached thereto. In such aspects, when the force is applied radially away from the insertion axis A, the finger 200 slidably moves along the body 154 such that the sliding surface 204 and the protrusion 208 are moved away from the insertion axis A. A biasing mechanism may be disposed between the finger 200 and the body 154, such that when the force is removed from the finger, the biasing mechanism moves the finger 200 back towards the insertion axis A. The biasing mechanism may be a helical spring, a deformable rod, or another mechanism configured to provide a biasing force against the finger 200 from the body 154.

The finger 200 may contact the shaft 14 to prevent the shaft 14 from being moved out of the shaft engagement socket 104. The shaft 14 may define a notch 26 that is configured to receive the protrusion 208 of the finger 200. The notch 26 may be a radial notch that extends around the circumference of the shaft 14, Alternatively, the notch 26 may be defied on a portion of the shaft 14 and not extend circumferentially around the shaft 14, The shaft 14 may include a plurality of notches 26. In some aspects, the number of notches 26 may be the same as the number of fingers 200.

The notch 26 may be arcuate and may complement the protrusion 208, such that the protrusion 208 may be moved into the notch 26. It will be appreciated that the specific dimensions of the notch 26 are not limited by this disclosure, and other shapes can be suitable, for example, triangular, square, semi-circular, or other shapes. The protrusion 208 may similarly include any suitable shape, for example, semi-circular, triangular, quarter-circular, or another suitable shape. While the protrusion 208 can be dimensioned to complement the notch 26, this is not a requirement. The specific dimensions of the notch 26 can vary, but it will be understood that the largest cross-sectional measurement of the shaft 14 at the notch 26 is smaller than the largest cross-sectional measurement of the shaft 14 between the notch 26 and the proximal end 16. For example, in shafts having a round cross section, the largest cross-sectional measurement is the diameter.

The notch 26 may be disposed between the proximal end 16 and the distal end 18. In some aspects, the notch 26 may be adjacent to the socketing region 20. As exemplified in FIG. 3, the notch 26 may be located along the shaft 14 between the socketing region 20 and the distal end 18.

When the protrusion 208 is within the notch 26, axial movement of the shaft 14 along the insertion axis A is precluded. This helps prevent the shaft 14 and the tool to which it is attached (not shown) from being removed from the shaft engagement socket 104. This decreases damage to the tool, injury to the user, and any preparation time required to re-insert or correct alignment of the tool in the retention assembly 100.

Figure 4:
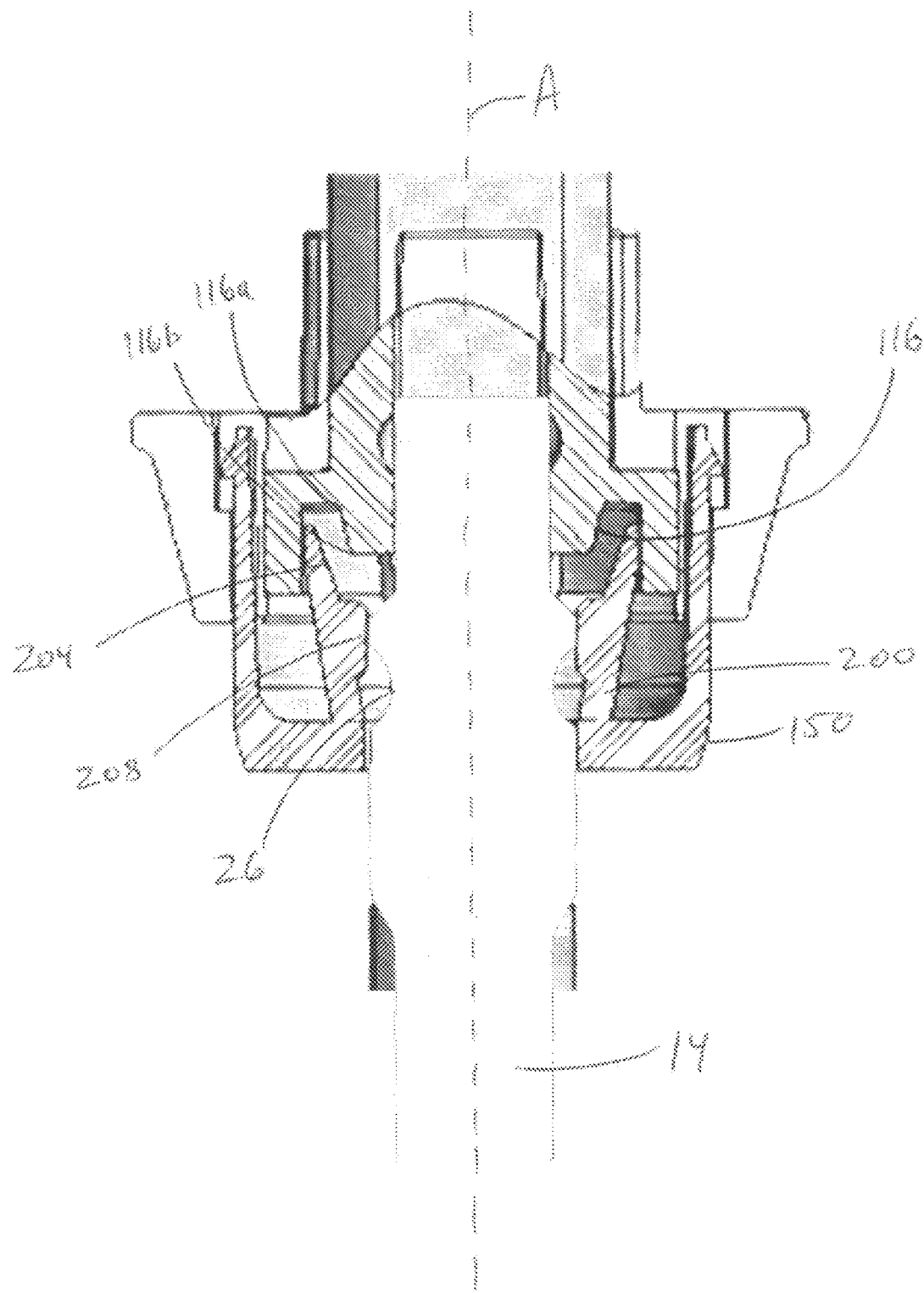
FIG. 4 illustrates a cross-sectional view of a shaft being received into a retention assembly.
Figure 5:
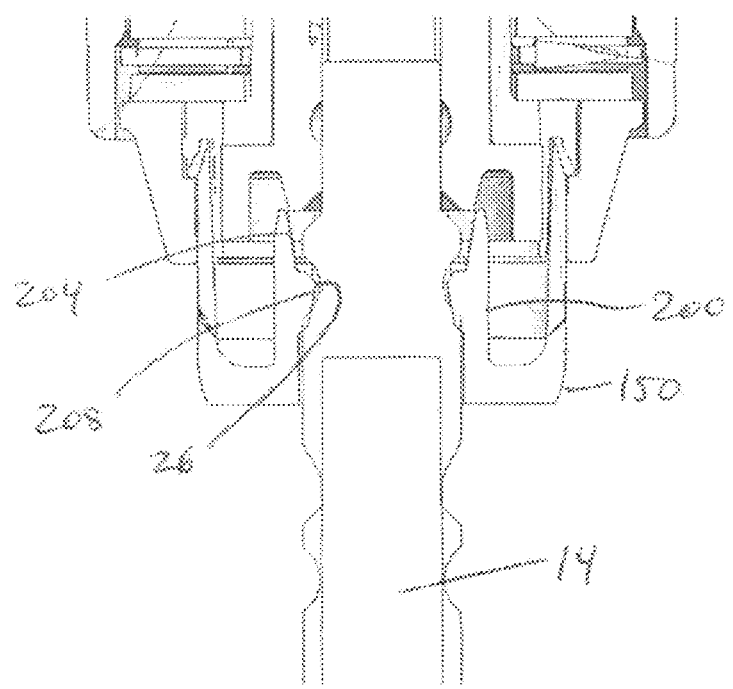
FIG. 5 illustrates the shaft being secured within the retention assembly of FIG. 4.

The retainer 150 is configured to permit the shaft 14 to pass along a first direction along the insertion axis A towards the shaft engagement socket. Referring to FIG. 4, as the shaft 14 is moved into the opening 158 of the retainer 150, the shaft 14 contacts the finger 200. This contact may occur at the proximal end 16 or at another location along the shaft 14 between the proximal end 16 and the notch 26. The shaft 14 may contact the protrusion 208 on the finger 200. As the shaft 14 moves through the opening 158, a force is exerted on the finger 200 radially away from the shaft 14 and the insertion axis A. This force results in the deflection of the finger 200 as described above, Referring now to FIG. 5, as the shaft 14 is moved further towards the shaft engagement socket 104, the socketing region 20 is positioned within the shaft receptacle 108. When the socketing region 20 is in the shaft receptacle 108, the notch 26 contacts the finger 200, preferably at the protrusion 208, The protrusion 208 disposed in the notch 26 prevents the shaft 14 from being moved in a second direction opposite the first direction and out of the shaft receptacle 108.

To remove the shaft 14 from the shaft receptacle 108, the finger 200 is deflected radially such that the shaft 14 does not contact the finger 200. The finger 200 may be deflected such that the protrusion 208 is moved out of the notch 26, After the finger 200 is moved away from the shaft 14, the shaft 14 is permitted to move axially along the insertion axis A and can be removed from the shaft engagement socket 104 and out of the retainer 150 through the opening 158.

Figure 17:
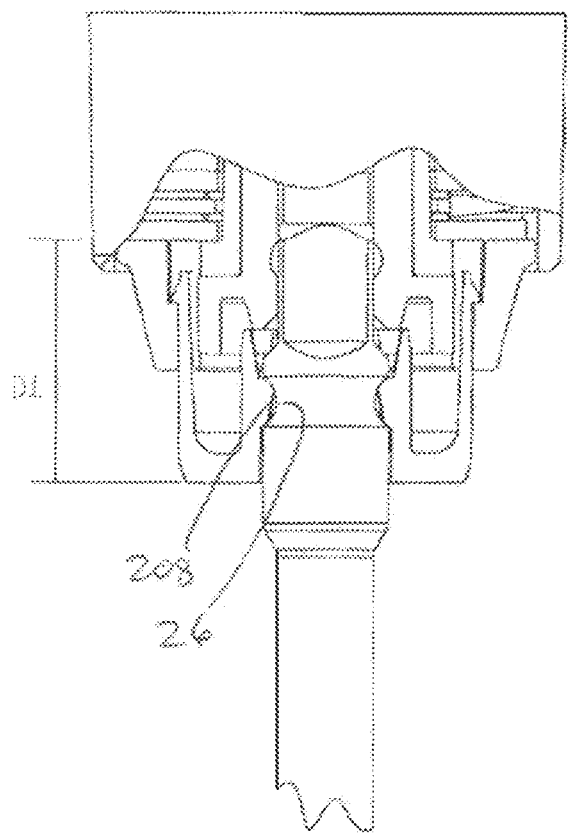
FIG. 17 illustrates a cross-sectional view of the retention assembly of FIGS. 14-16 with the retainer in the locking position, the shaft engaged in the shaft receptacle, and the fingers contacting the notch of the shaft.
Figure 18:
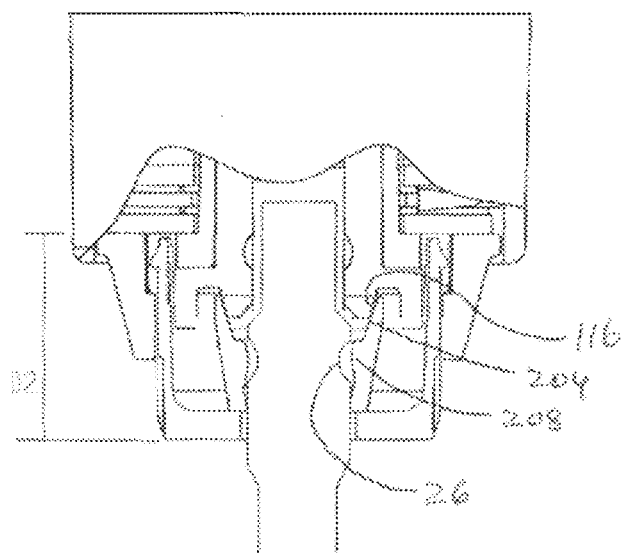
FIG. 18 illustrates a cross-sectional view of the retention assembly of FIGS. 14-17 with retainer in an unlocking position and the fingers deflected radially according to an aspect of the present disclosure.

The finger 200 may be deflected by an actuator, such as a button or a lever. In some aspects, the finger 200 may be pushed radially away from the insertion axis A by another component of the retention assembly 100. In some aspects, the retainer 150 may be movable axially along the insertion axis A toward and away from the shaft engagement socket. As shown in FIG. 17, the retainer 150 may have a locking position when the retainer 150 is at a first distance D1 away from the shaft engagement socket. Referring to FIG. 18, the retainer 150 may have an unlocking position when the retainer 150 is at a second distance D2 away from the shaft engagement socket. The second distance is smaller than the first distance. When the retainer 150 is in the locking position and the shaft 14 is inserted in the shaft receptacle 108, the finger 200 contacts the shaft 14 and prevents the shaft 14 from being removed from the shaft receptacle 108. When the retainer 150 is in the unlocking position, the finger 200 is deflected away from the shaft 14 and the shaft 14 can be axially moved out of the shaft receptacle 108.

Referring to FIG. 4, the shaft engagement socket 104 may include a ramp 116 configured to slidably contact the sliding surface 204 of the finger 200. The ramp 116 has a proximal end 116a and a distal end 116b opposite the proximal end 116a. The ramp 116 is oriented such that the distal end 116b is closer to the insertion axis A than the proximal end 116a. When the retainer 150 is moved from the locking position to the unlocking position, the sliding surface 204 contacts the ramp 116, and the finger 200 slides along the ramp 116 toward the proximal end 116a. As the finger 200 slides along the ramp 116, the finger 200 is deflected radially away from the insertion axis A and away from the notch 26. To move the retainer 150 to the locking position, the retainer 150 may be translated in the second direction away from the shaft engagement socket 104 such that the finger 200 slides along the ramp 116 towards the distal end 116b.

In some aspects, a biasing mechanism may be disposed between the retainer 150 and the shaft engagement socket 104. The biasing mechanism may be a spring, a deformable rod, or another suitable mechanism that is configured to provide a biasing force. The retainer 150 may be biased toward the locking position, such that moving the retainer 150 from the locking position to the unlocking position requires overcoming the biasing force exerted by the biasing mechanism on the retainer.

In some aspects, the finger 200 acts as the biasing mechanism. When the sliding surface 204 is moved along the ramp 116 towards the proximal end 116a, the finger 200 is deflected. The finger 200 may be biased against this deflection such that the retainer 150 is configured to move from the unlocking position to the locking position absent a suitable force exerted on the retainer 150 to move the retainer 150 to the locking position or keep the retainer 150 in the locking position.

The retainer 150 may be attached to the shaft engagement socket 104 via any suitable method that permits axial movement of the retainer 150 relative to the shaft engagement socket 104 along the insertion axis A. The retainer 150 may have an outer wall 166 extending from the body 154. The outer wall 166 may include an attachment clip 170 configured to engage with the shaft engagement socket 104. The attachment clip 170 is an exemplary only, and a snap-in or removable fit is not an exclusive means of attachment. The attachment clip 170 may or may not have one or more heads 172. An exemplary attachment clip 170 without heads is depicted in FIG. 19. In some aspects, the outer wall 166 may define a plurality of attachment clips 170 disposed around the circumference of the retainer 150.

The shaft engagement socket 104 may define a channel 120 configured to receive the attachment clip 170. The channel 120 has a floor 124 and a ceiling 128. The attachment clip 170 has a head 172 disposed within the channel 120 and configured to move between the floor 124 and the ceiling 128. The channel 120 may be a continuous channel that surrounds the shaft engagement socket 104, and the attachment clip 170 may be configured to move within the channel 120 around the insertion axis A. This would permit the retainer 150 to rotate freely around the insertion axis A.

The attachment clip 170 may be removed from the channel 120 such that the retainer 150 is separated from the shaft engagement socket 104, The attachment clip 170 may be deflected toward the insertion axis A such that the head 172 can be removed from within the channel 120 through a channel opening 122 between the channel floor and the insertion axis A. Alternatively, if the channel floor 124 is between the channel opening 122 and the insertion axis A, the attachment clip 170 may be deflected away from the insertion axis A such that the head 172 can be removed from the channel 120.

The shaft engagement socket 104 defines a first interface 123 shown as a circumferential end that is configured to engage a second interface 152 disposed on the retainer 150 between the heads 172. In some instances, the retainer 150 does not have any heads 172, and the first interface 123 can interface with the second interface 152 circumferentially as depicted in FIGS. 19 and 20.

As described above, the retainer 150 may axially move along the insertion axis A toward and away from the shaft retention socket 104. The distance that the retainer 150 may move may be limited by the size of the channel 120 and the head 172 of the attachment clip 170. When the head 172 is in contact with the floor 124 of the channel 120, the retainer 150 may be at its maximum distance from the shaft retention socket 104, and when the head 172 is in contact with the ceiling 128, the retainer 150 may be at its minimum distance from the shaft retention socket 104. It will also be understood that the retainer 150 may be positioned between the maximum and minimum distances.

Those of ordinary skill in the art will recognize that the attachment clip is not intended to be a limitation, nor is it the singular means of attachment.

The amount of force required to move the retainer 150 from the locking position to the unlocking position may be varied depending on the desired applications. To allow the shaft 14 to be removed from the retention assembly 100, the finger 200 should be deflected such that it does not contact the shaft 14. Preferably, the finger 200 should be deflected to move the protrusion 208 out of the notch 26. To remove the finger 200 from the shaft, the finger 200 can be deflected by a minimal deflection distance. The greater the minimal deflection distance, the more force will be required to deflect the finger 200 to remove it from contacting the shaft 14. To reduce the required force of moving the retainer from the locking position to the unlocking position, the minimal deflection distance can be reduced. The minimal deflection distance may be decreased by various methods, and this disclosure is not limited by any particular method. Suitable methods include decreasing the thickness of the finger 200, forming the finger 200 out of a more malleable material, reducing the size of the protrusion 208, and disposing the finger 200 radially farther away from the insertion axis A. Conversely, to increase the force required to move the finger 200 the minimal deflection distance, the finger 200 may be thicker, may include a more rigid material, and may be positioned closer to the insertion axis A.

Figure 6:
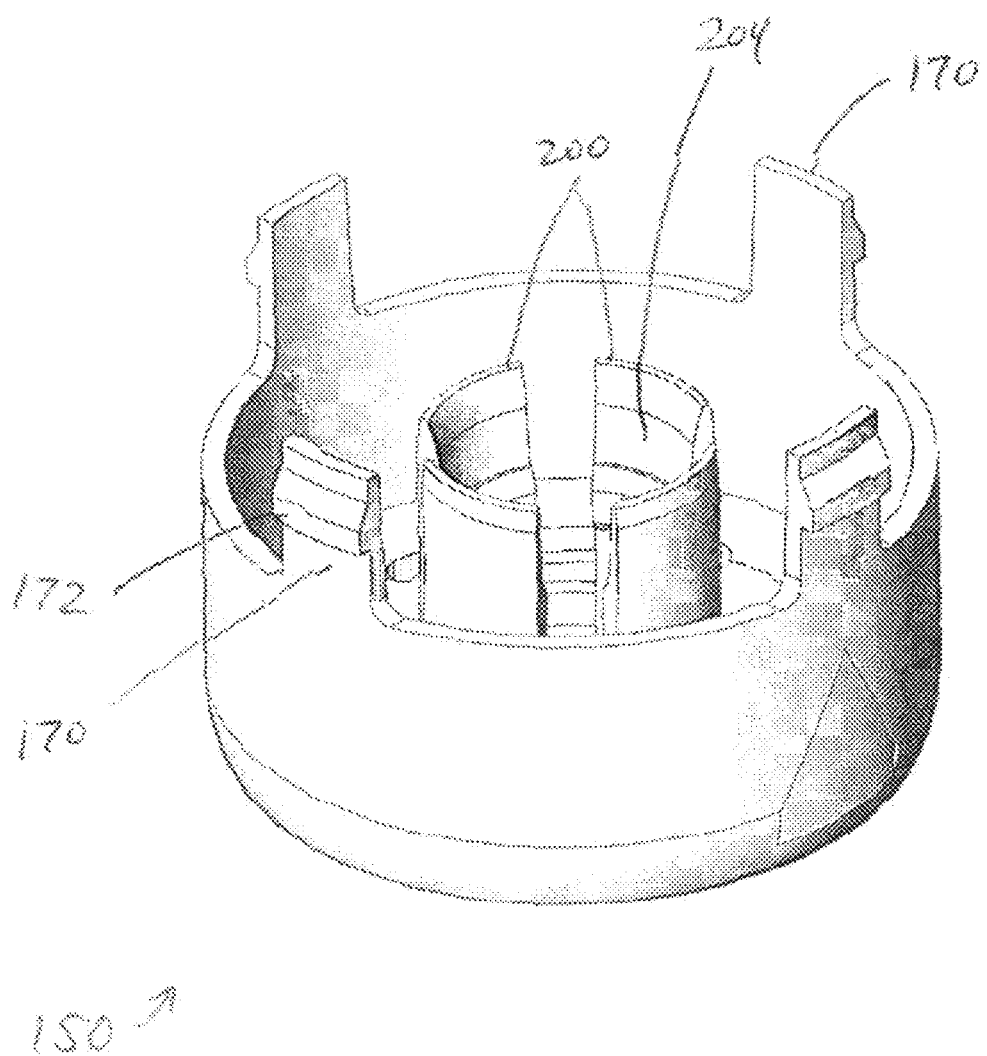
FIG. 6 illustrates a top isometric view of a retainer according to an aspect of the present disclosure.
Figure 7:
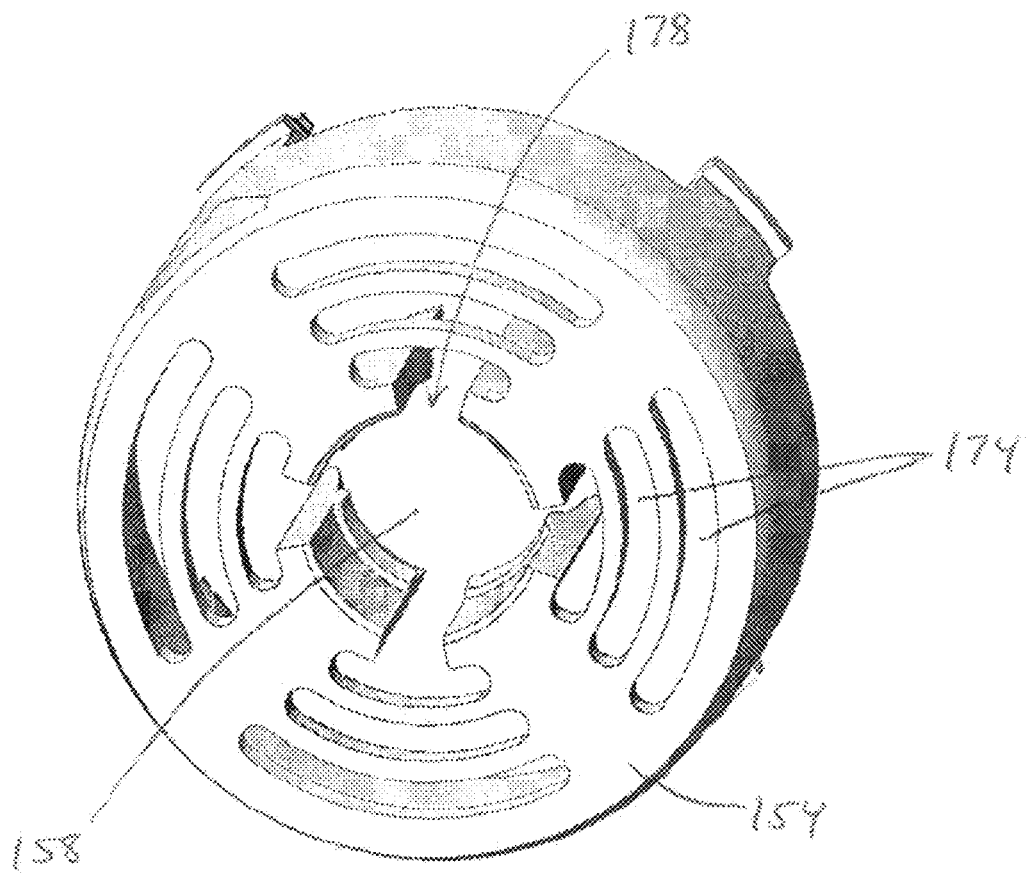
FIG. 7 illustrates a bottom isometric view of the retainer of FIG. 6.
Figure 8:
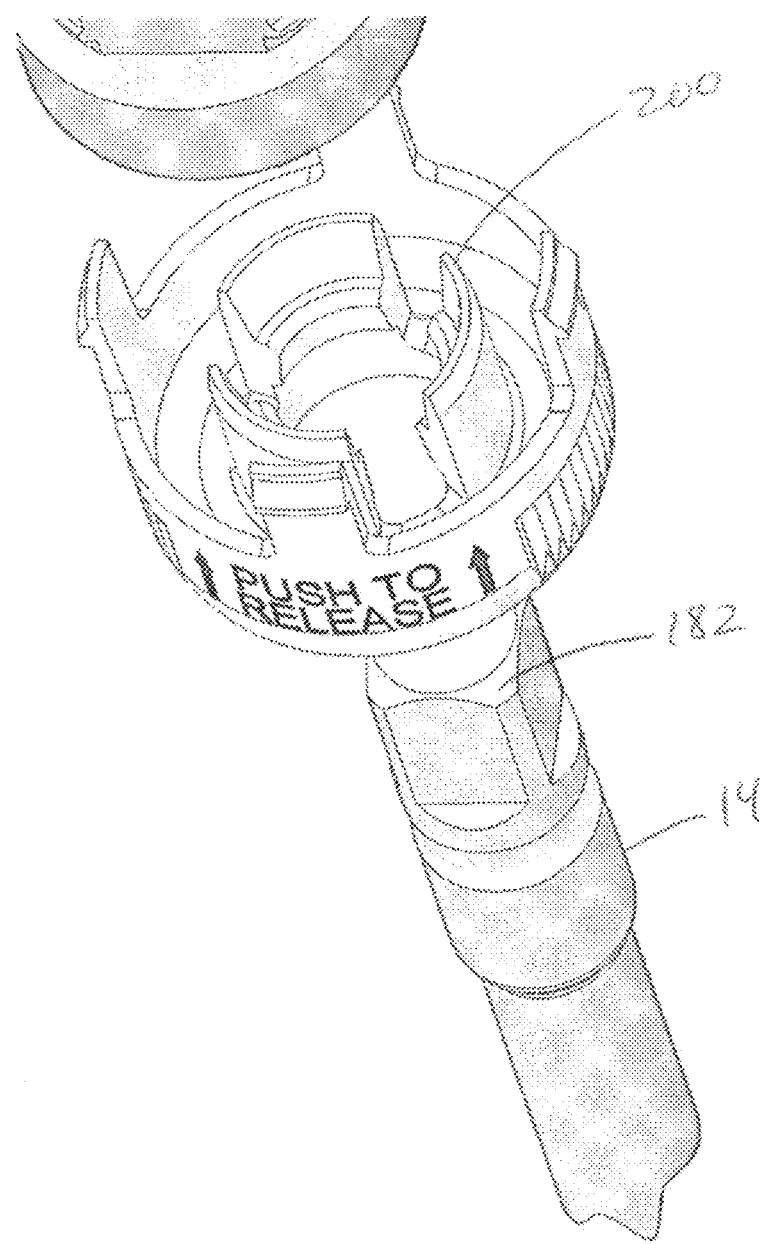
FIG. 8 illustrates an exploded isometric view of a retention assembly according to an aspect of the disclosure.

In some aspects, for example as shown in FIGS. 9-12, the body 154 of the retainer 150 may be a solid and rigid component. In other aspects, the body 154 may be configured to deflect when the finger 200 deflects. As seen in FIGS. 6 and 7, the body 154 may define one or more cutouts 174. The cutouts 174 may be cavities that extend through the body 154, or they may be indentations in the body 154 that do not extend all the way through the body 154. The cutouts 174 allow the body 154 to operate as a spring and deform radially away from the insertion axis A when the finger 200 is deflected in the same direction. The amount of deformation may be varied. For example, to increase deformation, more cutouts 174 may be present between the opening 158 and the outer wall 166, the cutouts 174 may be larger (thus reducing the size of the body 154), or the cutouts 174 may be positioned to reduce the amount of force required to deform the body 154. Conversely, to decrease deformability of the body 154, fewer or no cutouts 174 may be present, the cutouts 174 may be smaller, or the cutouts 174 may be disposed to increase rigidity of the body 154.

Referring to FIGS. 6 and 7, the retainer 154 may include four fingers 200 and a plurality of cutouts 174. The cutouts 174 may be disposed directly orthogonal to each finger 200 and be linearly between each finger 200 and the outer wall 166. The cutouts 174 may be offset such that they are orthogonal to the space shown between each finger 200 and are between that space and the outer wall 166. In some aspects, some cutouts 174 may be positioned orthogonal to the finger 200, while other cutouts 174 may be positioned orthogonal to the space between adjacent fingers 200.

The cutouts 174 may be round, oblong, rectangular, arcuate, S-shaped, zig-zag, or another suitable shape, and this disclosure is not limited to any particular dimension of the cutouts 174. The retainer 150 may include one or more cutouts 174 of the same shapes and dimensions, or the retainer 150 may include cutouts 174 having different shapes and dimensions.

Figure 9:
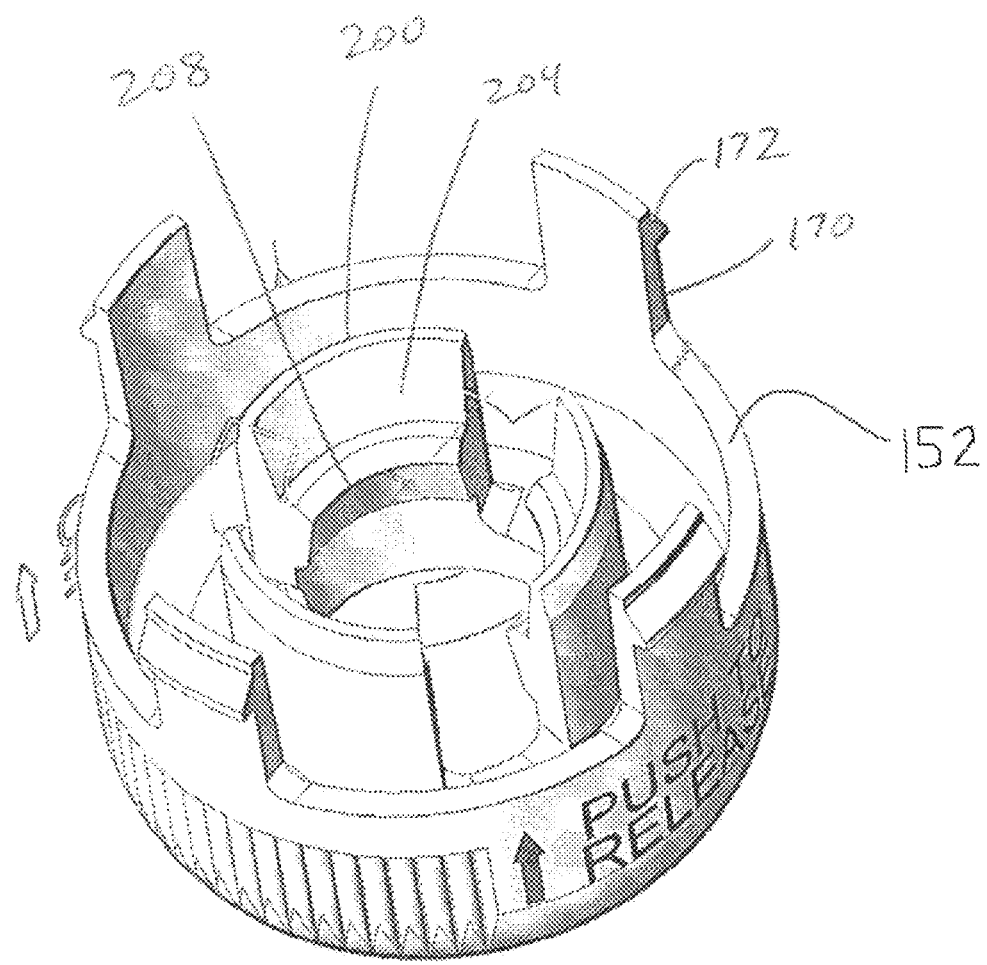
FIG. 9 illustrates a top isometric view of a retainer according to another aspect.
Figure 10:
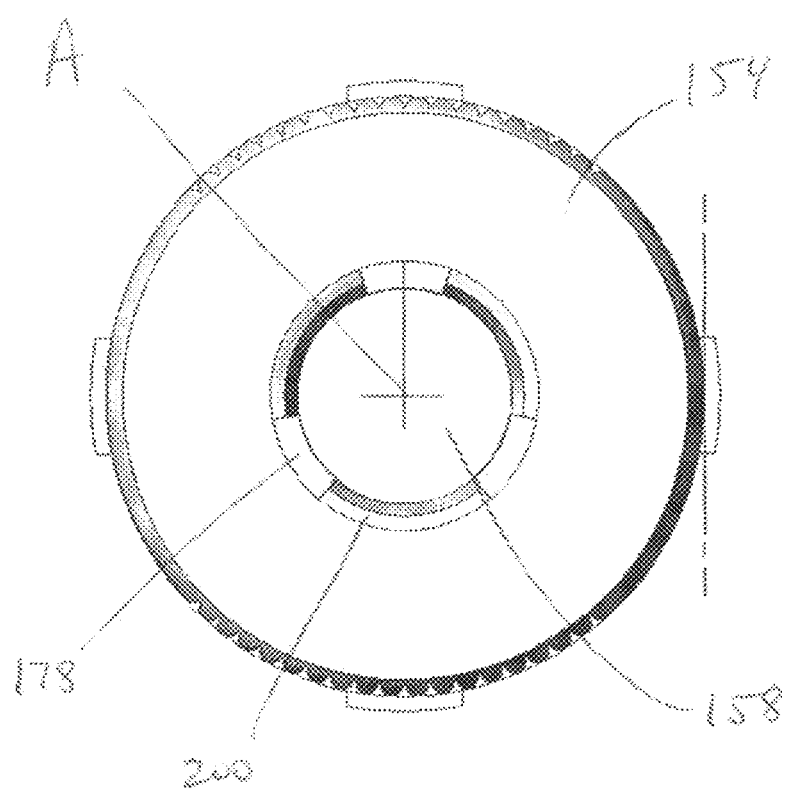
FIG. 10 illustrates a bottom perspective view of the retainer of FIG. 9.
Figure 11:
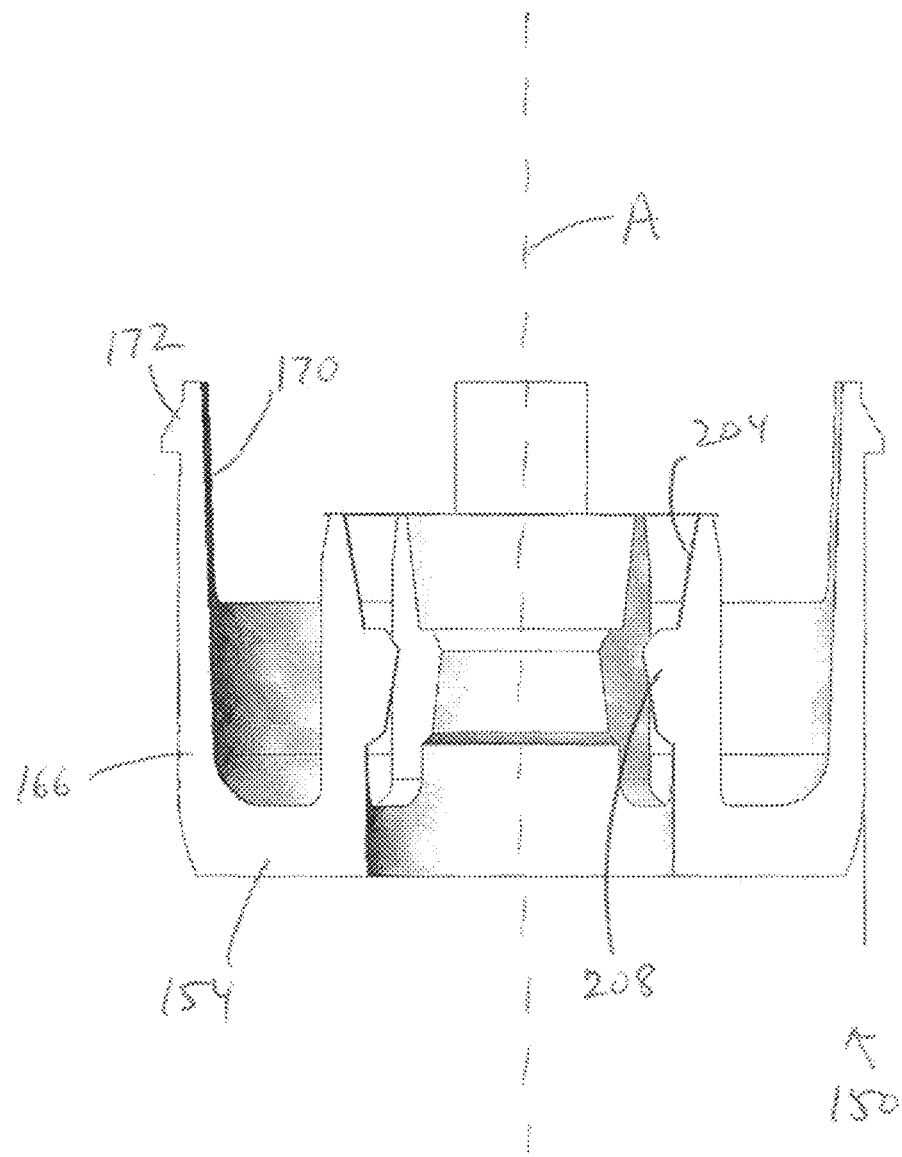
FIG. 11 illustrates a cross-sectional view of the retainer of FIGS. 9 and 10 with fingers not deflected.
Figure 12:
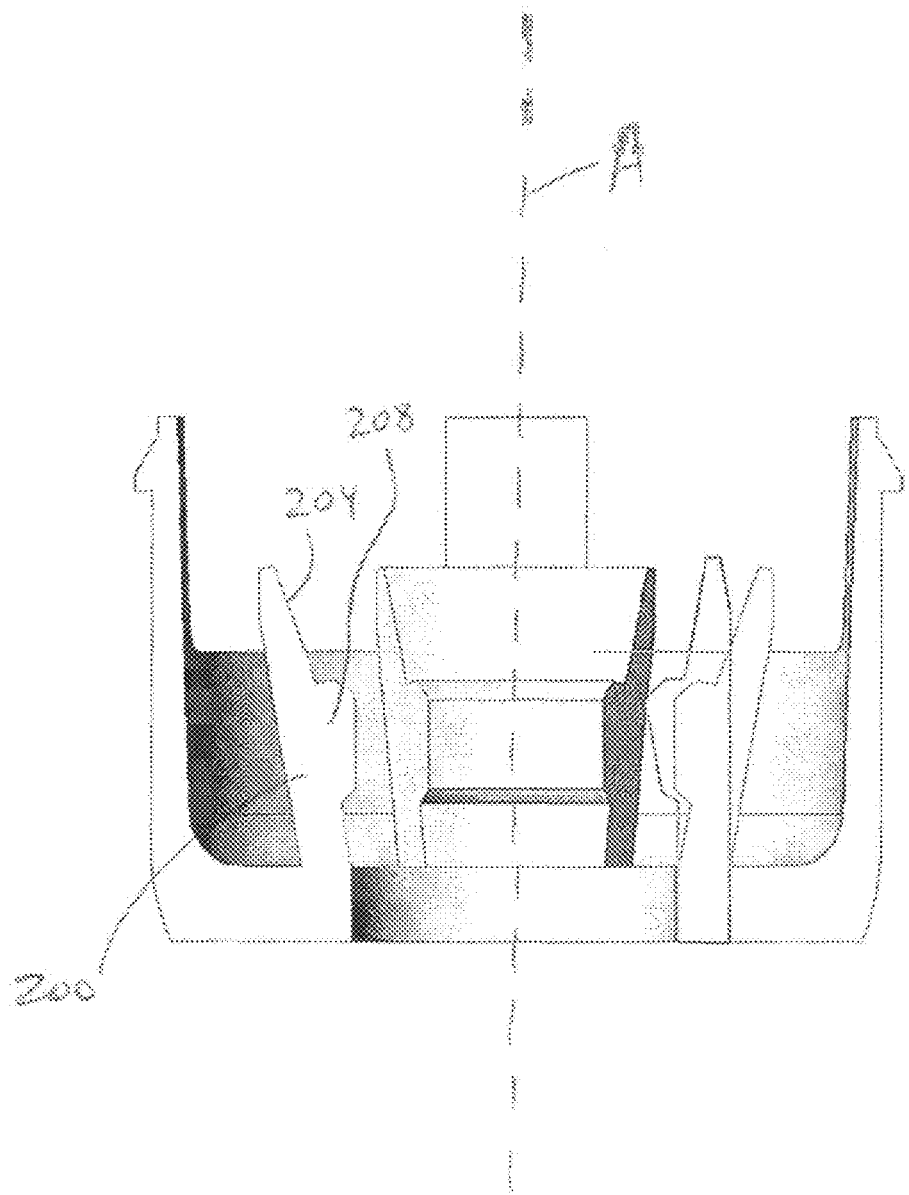
FIG. 12 illustrates a cross-sectional view of the retainer of FIGS. 9-11 with fingers deflected radially.

Although FIG. 9 depicts a solid body 154 and three fingers 200 while FIG. 7 depicts a body 154 having cutouts 174 and four fingers 200, it will be understood that the arrangements are interchangeable and are not limited to the exemplified drawings. For example, a retainer 150 having a solid body 154 may have four fingers 200, and a retainer 150 having a body 154 with cutouts 174 may have three fingers 200. Other combinations of components and number of fingers 200 may exist as well, and the disclosure is not limited to only the exemplified drawings.

In some aspects, it may be advantageous to ensure that the shaft 14 is moved into the retention assembly 100 at a specific angle and orientation. If the shaft 14 is inserted into the opening 158 at an improper angle, the retainer 150 may be damaged. For example, one or more fingers 200 may be deformed or broken. In some aspects, the shaft 14 may not be engaged with the shaft engagement socket 104 properly, leading to poor connection to the base 10 and to inadequate use of the connected tool.

To improve the engagement of the shaft 14 with the retention assembly 100, one or more guides 178 may be disposed on the retainer 150. When the shaft 14 is moved into the opening 158, the proximal end 16 of the shaft 14 contacts the one or more guides 178. As the shaft 14 moves through the opening 158, the shaft 14 is oriented to the desired angle relative to the insertion axis A. In sonic aspects, the proximal end 16 of the shaft 14 may include a keyed portion 182 configured to complement the guides 178, such that the shaft 14 is permitted to pass through the guides 178 and enter the opening 158 only when the shaft 14 is in the desired orientation. Conversely, if the shaft 14 is not oriented in the desired orientation such that the keyed portion 182 corresponds to the guides 178, then the shaft 14 may not be permitted from passing into the retainer 150. The keyed portion 182 may be defined by the one or more locking surfaces 22 at the socketing region 14. The guides 178 may be gaps between adjacent fingers 200, for example, as shown in FIG. 7. In such aspects, the keyed portion 182 may be dimensioned to correspond to the gaps such that the shaft 14 can be inserted into the retainer 150 only when the keyed portion 182 aligns with the gaps.

Although the guides 178 are depicted in FIG. 7 showing a retainer 150 having four fingers 200, it will be understood that the guides 178 as described above can be used with retainers having one, two, three, or any other suitable number of fingers 200. For example, the retainer 150 depicted in FIG. 9 that has three fingers 200 may include one or more guides 178 as described.

Figure 13:
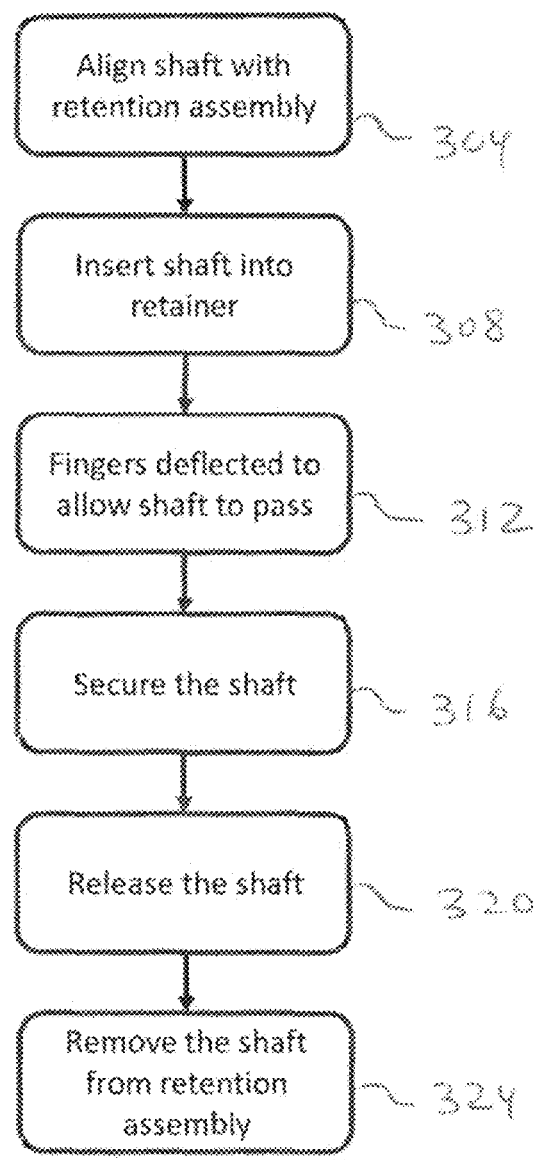
FIG. 13 illustrates a flowchart depicting a method of engaging a shaft with a retention assembly according to an aspect of the disclosure.
Figure 14:
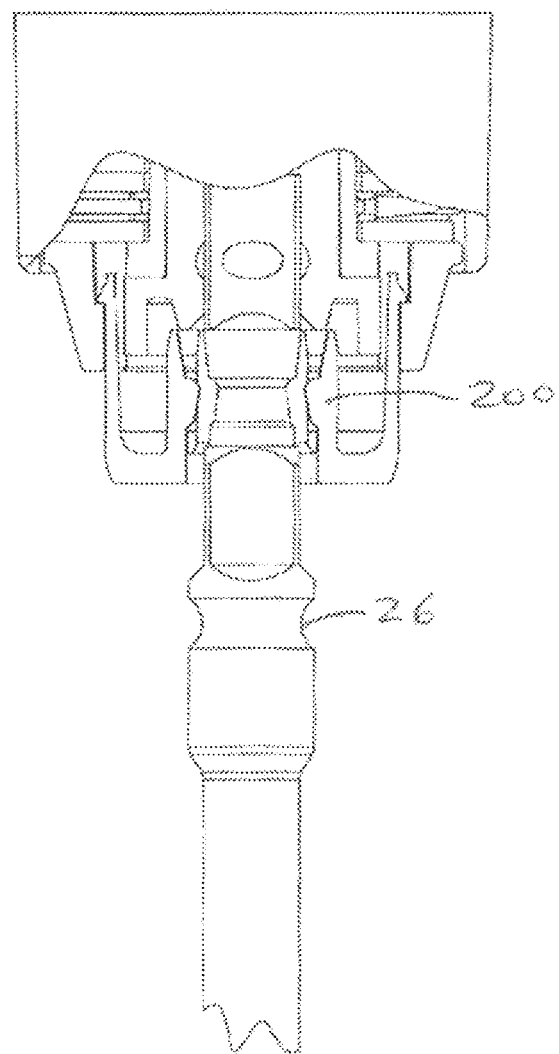
FIG. 14 illustrates a cross-sectional view of a retention assembly according to an aspect of the disclosure showing a shaft being introduced into the retention assembly.
Figure 15:
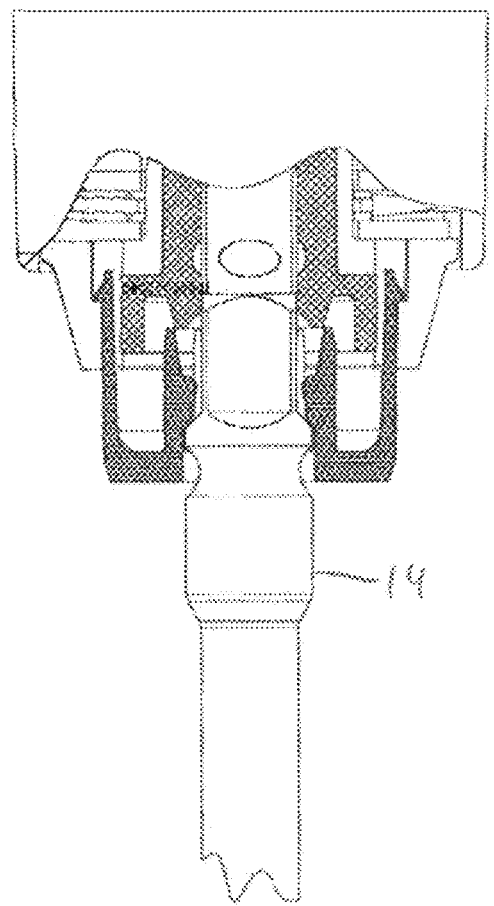
FIG. 15 illustrates a cross-sectional view of the retention assembly of FIG. 14 with the shaft contacting the fingers of the retention assembly.

An exemplary method 300 of engaging a shaft 14 with the retention assembly 100 is depicted in the flowchart of FIG. 13. First, as shown in step 304, the shaft 14 is aligned with the opening 158 of the retainer 150. The alignment step may include orienting the shaft 14 such that the keyed portion 182, if present, engages with the guide 178. This is exemplified in FIG. 14. Then, in step 308, the shaft 14 is moved axially along insertion axis A towards the shaft engagement socket 104. The shaft 14 contacts the finger 200, for example, at the protrusion 208. This is shown in FIG. 15.

An alternative connection between the shaft engagement socket 104 and the retainer 150 is presented in FIGS. 19 and 20. This alternative illustrates a means to attach the retainer 150 to the shaft engagement socket 104 via the first interface 123 and the second interface 152. The interfaces form a connection. The connection may be a fixation means. A non-exclusive list includes latches and catches, friction, threaded, sonic weld, adhesive, glue, and the like. The fixation means functions to fix the shaft engagement socket 104 and the retainer 150 together either temporarily or permanently depending on the intended use.

Figure 16:
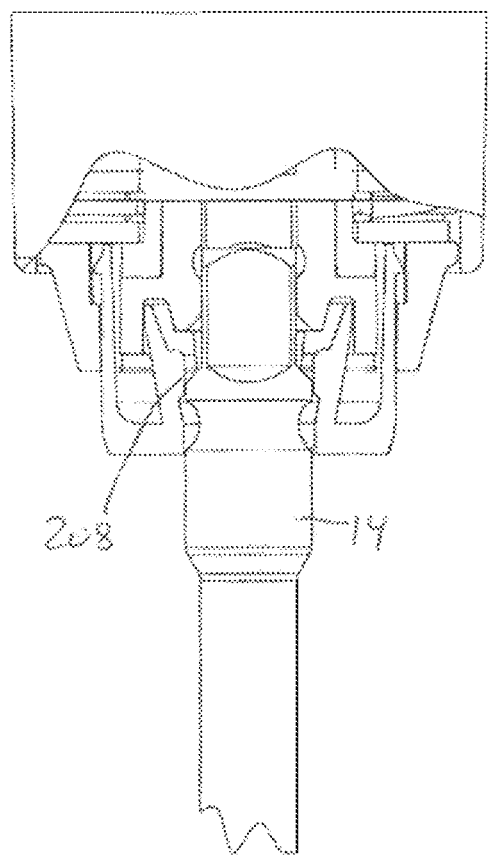
FIG. 16 illustrates a cross-sectional view of the retention assembly of FIGS. 14 and 15 with the shaft causing the fingers to deflect radially.

As the shaft 14 continues to be moved along the insertion axis A, the shaft 14 forces the fingers 200 to radially deflect away from the shaft 14 and the insertion axis A in step 312 and as shown in FIG. 16. The shaft 14 is then moved past the fingers 200 and the protrusions 208 such that the notch 26 contacts the fingers 200, preferably at the protrusion 208, In step 316, the protrusions 208 engage with the notch 26. At this point, the socketing region 20 is in the shaft receptacle 108 and engaged with the shaft engagement socket 104, and the shaft 14 is secured to the retention assembly 100. This is depicted in FIG. 17. In an optional step 320, to remove the shaft 14 from the retention assembly 100, the retainer 150 may be moved axially towards the shaft engagement socket 104 until the fingers 200 contact the shaft engagement socket 104 at the ramp 116. As shown in FIG. 18, the sliding surface 204 of the finger 200 slides along the ramp 116 toward the proximal end 116a of the ramp 116. This sliding forces the fingers 200 to deflect radially away from the shaft 14 such that the fingers 200 do not contact the notch 26 and the protrusions 208 are moved out of the notch 26. After this, in an optional step 324, the shaft 14 may be removed axially along the insertion axis A away from the shaft engagement socket 104 and removed from the retention assembly 100 altogether.

The retainer 150 may include different materials. Alternatively, the retainer 150 may be a unitary integrated piece comprised of a uniform material. Materials may include metals, plastics, and resins. In sonic aspects, the retainer 150 may include polypropylene, polytetrafluoroethylene (PTFE), polyethylene, or another suitable plastic. It will be appreciated that in aspects of this disclosure used in the medical field, the plastic needs to be suitable for medical use.

The retainer 150 may be designed and intended to be disposable after a limited number of uses. In some aspects, the retainer 150 may be designed to be disposed after a single use. The disposability is advantageous because it allows the retainer 150 to be manufactured out of cheaper materials. In aspects where the retainer 150 is intended to be disposable, the retainer 150 is formed of materials that are not designed for heat sterilization that would otherwise be necessary to reuse medical devices. In such aspects, instead of sterilizing the retainer 150 and reusing it, the retainer 150 is disposed of and a new retainer 150 is implemented.

While systems and methods have been described in connection with the various embodiments of the various figures, it will be appreciated by those skilled in the art that changes could be made to the embodiments without departing from the broad inventive concept thereof. It is understood, therefore, that this disclosure is not limited to the particular embodiments disclosed, and it is intended to cover modifications within the spirit and scope of the present disclosure as defined by the claims.

What is claimed is:

1. A retention assembly for connecting a base to a tool having a shaft, the retention assembly comprising:
   a shaft engagement socket defining a shaft receptacle configured to receive the shaft along an insertion axis;
   a retainer configured to releasably secure the shaft to the shaft engagement socket, the retainer having a body that defines an opening extending therethrough, the opening being dimensioned to receive the shaft; and
   at least one finger extending from the body of the retainer, the at least one finger defining a sliding surface and being configured to contact the shaft,
   wherein the sliding surface of the at least one finger is configured to slidably contact a ramp on the shaft engagement socket;
   wherein the retainer is configured to translate relative to the shaft engagement socket along the insertion axis, such that when the retainer is translated toward the shaft engagement socket, the sliding surface of the at least one finger slides along the ramp of the shaft engagement socket and causes the at least one finger to move away from the shaft, and when the retainer is translated away from the shaft engagement socket, the sliding surface of the at least one finger slides along the ramp and causes the at least one finger to move towards the shaft; and wherein the retainer defines a guide configured to contact the shaft and to align the shaft to a permitted orientation, such that the shaft is precluded from moving through the retainer if the shaft is not in the permitted orientation.

2. The retention assembly of claim 1, wherein the at least one finger further includes a protrusion between the sliding surface and the body of the retainer, the protrusion extending from the at least one finger towards the insertion axis and configured to be received within a notch on the shaft, such that when the protrusion is in the notch, the shaft is precluded from moving along the insertion axis.

3. The retention assembly of claim 2, wherein the protrusion is triangular and the notch on the shaft is triangular.

4. The retention assembly of claim 2, wherein the protrusion is arcuate and the notch on the shaft is arcuate.

5. The retention assembly of claim 1, wherein the at least one finger is deformable such that when the retainer is translated towards the shaft engagement socket, the at least one finger deflects radially away from the insertion axis.

6. The retention assembly of claim 1, wherein the retainer includes a plurality of fingers.

7. The retention assembly of claim 6, wherein the retainer includes at least two fingers.

8. A retention assembly for connecting a base to a tool having a shaft, the retention assembly comprising:
a shaft engagement socket defining a shaft receptacle configure to receive the shaft along an insertion axis;
a retainer configured to releasably secure the shaft to the shaft engagement socket, the retainer having a body that defines an opening extending therethrough, the opening being dimensioned to receive the shaft; and
at least one finger extending from the body of the retainer, the at least one finger defining a sliding surface and being configured to contact the shaft,
wherein the sliding surface of the at least one finger is configured to slidably contact a ramp on the shaft engagement socket;
wherein the retainer is configured to translate relative to the shaft engagement socket along the insertion axis, such that when the retainer is translated toward the shaft engagement socket, the sliding surface of the at least one finger slides along the ramp of the shaft engagement socket and causes the at least one finger to move away from the shaft, and when the retainer is translated away from the shaft engagement socket, the sliding surface of the at least one finger slides along the ramp and causes the at least one finger to move towards the shaft;
wherein the retainer includes an outer wall extending from the body and a deformable clip disposed on the outer wall, the deformable clip being configured to slidably engage the shaft engagement socket to releasably secure the retainer to the shaft engagement socket; and
wherein the shaft engagement socket includes four walls, each wall being orthogonal to two adjacent walls, the four walls defining the shaft receptacle being configured to receive the shaft, wherein the proximal end of the shaft having a rectangular cross section and wherein the shaft engagement socket is configured to contact a locking surface on a socketing region of the shaft when the socketing region is in the shaft engagement socket, such that when the wall is in contact with the locking surface, rotational movement of the shaft around the insertion axis is precluded and wherein the socketing region is shaped to correspond to the cross-section of the shaft.

9. The retention assembly of claim 8, wherein the body of the retainer includes a cutout between the at least one finger and the outer wall.

10. The retention assembly of claim 9, wherein the body includes a plurality of cutouts between the at least one finger and the outer wall.

11. The retention assembly of claim 8, wherein the shaft engagement socket defines a radial channel having a floor and a ceiling, the radial channel being configured to receive an attachment clip therein, the attachment clip being movable within the channel between the floor and the ceiling, such that the movement of the retainer towards the shaft engagement socket is confined by contact between the attachment clip and the ceiling, and movement away from the shaft engagement socket is confined by contact between the attachment clip and the floor.

* * * * *